United States Patent [19]
Homan et al.

[11] Patent Number: 5,492,005
[45] Date of Patent: Feb. 20, 1996

[54] SYSTEM AND METHOD FOR DETERMINING DEPOSIT FORMATION AND MITIGATION BY FUEL ADDITIVES

[75] Inventors: Howard S. Homan, Piscataway; Allan C. Schott, Washington, both of N.J.

[73] Assignee: Exxon Research and Engineering Company, Florham Park, N.J.

[21] Appl. No.: 334,704

[22] Filed: Nov. 4, 1994

Related U.S. Application Data

[63] Continuation of Ser. No. 116,176, Sep. 2, 1993, abandoned.

[51] Int. Cl.[6] .......................... G01N 11/00; G01N 25/02
[52] U.S. Cl. ...................... 73/61.62; 73/61.65; 73/53.05
[58] Field of Search ................................ 73/61.62, 61.65

[56] References Cited

U.S. PATENT DOCUMENTS

| | | | |
|---|---|---|---|
| 2,931,219 | 4/1960 | Moorman et al. | 73/61.62 |
| 3,059,467 | 10/1962 | Meguerian et al. | 73/61.62 |
| 3,108,468 | 10/1963 | Mickel | 73/61.62 |
| 3,438,248 | 4/1969 | Taylor et al. | 73/61.62 |
| 3,457,776 | 7/1969 | Cook | 73/61.62 |
| 4,910,999 | 3/1990 | Eaton | 73/61.62 |
| 5,287,731 | 2/1994 | Florkowski et al. | 73/53.05 |
| 5,299,449 | 4/1994 | Hardy et al. | 73/61.62 |

FOREIGN PATENT DOCUMENTS

| | | | |
|---|---|---|---|
| 0297742 | 12/1987 | Japan | 73/61.62 |
| 0940024 | 7/1982 | U.S.S.R. | 73/61.62 |

Primary Examiner—Hezron E. Williams
Assistant Examiner—J. David Wiggins
Attorney, Agent, or Firm—Ronald D. Hartman

[57] ABSTRACT

The invention is a system and method to rate fuels and fuel additives for their tendency to form and mitigate intake system deposits in engines.

12 Claims, 6 Drawing Sheets

SYSTEM AND METHOD FOR DETERMINING DEPOSIT FORMATION AND MITIGATION BY FUEL ADDITIVES

This is a continuation, of application Ser. No. 116,176 filed Sept. 2, 1993 now abandoned.

BACKGROUND OF THE INVENTION

The present invention relates to a system for rating fuel and/or fuel additives for their tendency to form and mitigate deposits on solid surfaces. One problem addressed by this system is intake system deposits of internal combustion engines. Intake system deposits cause operational problems.

Engine tests of deposit mitigation by fuels and fuel additives are necessary but are laborious and time consuming. So, a rapid laboratory test, which ranks fuels and fuel additives in the order of deposit mitigation is of considerable value. The present invention is a new way to make and study deposits from fuels and lubricants. It is unique because its operating conditions can be changed to emulate the surface temperature fluctuations and fuel transport behavior of engine intake systems.

SUMMARY OF THE INVENTION

The present invention is a system and method to rate fuels and fuel additives for the formation of deposits. The system includes an optional enclosure, a solid block (hereinafter called a "nub") having a deposit surface within the enclosure, means for controlling magnitude and duration of the temperature of the deposit surface, means for introducing fuel and/or fuel additives into the enclosure onto the surface, and means for introducing gas into the enclosure if an enclosure is present. If the enclosure is omitted, then the deposits are, of course, in air. With an enclosure, the test may be performed in air or some other gas.

The nub is weighed before and after fuel is placed onto the deposit surface. The change in nub weight indicates the fuel and/or fuel additives propensity to leave deposits.

DESCRIPTION OF THE PREFERRED EMBODIMENT

Figure 1A:
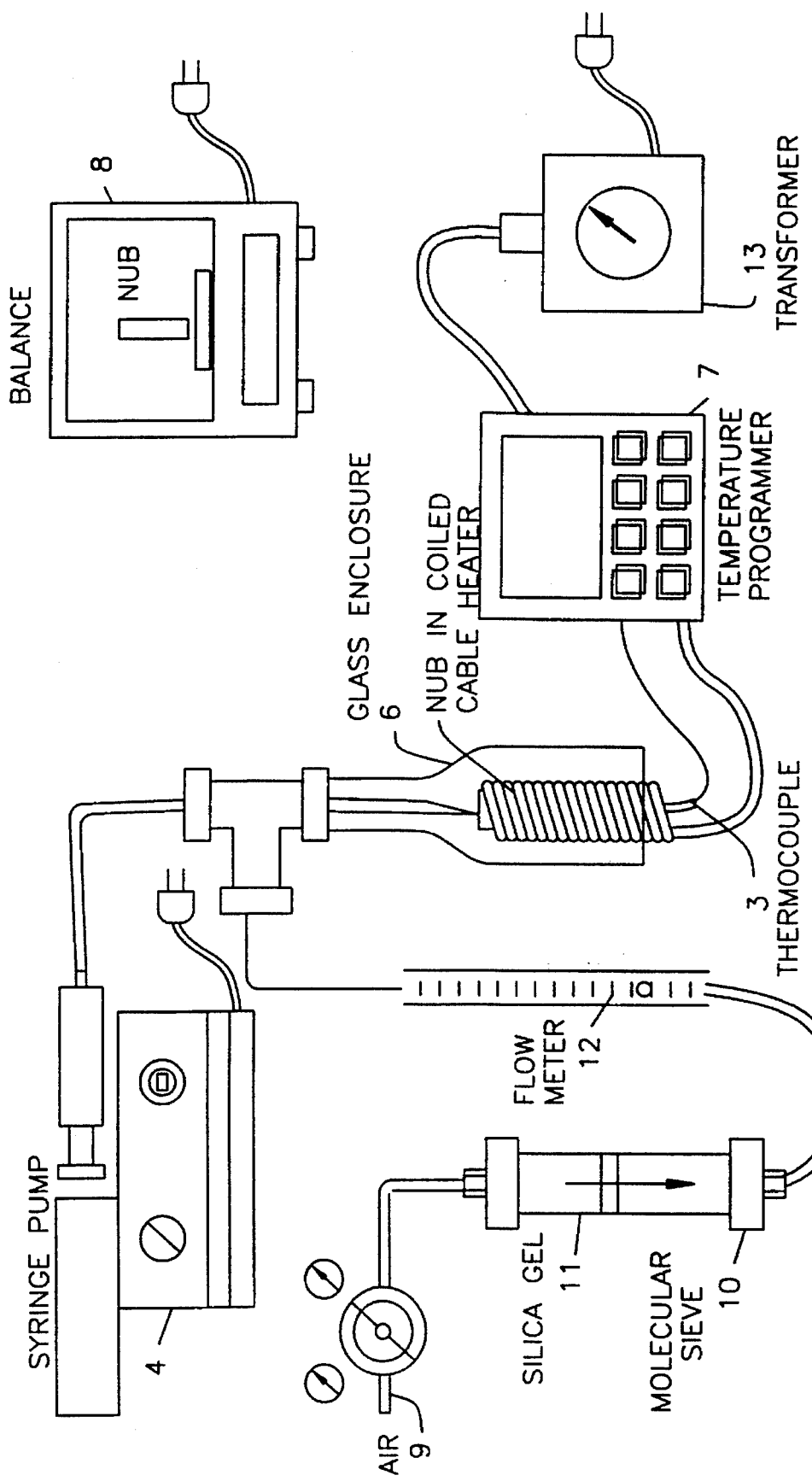
FIGS. 1A and 1B show a schematic diagram of the system of the present invention.
Figure 1B:
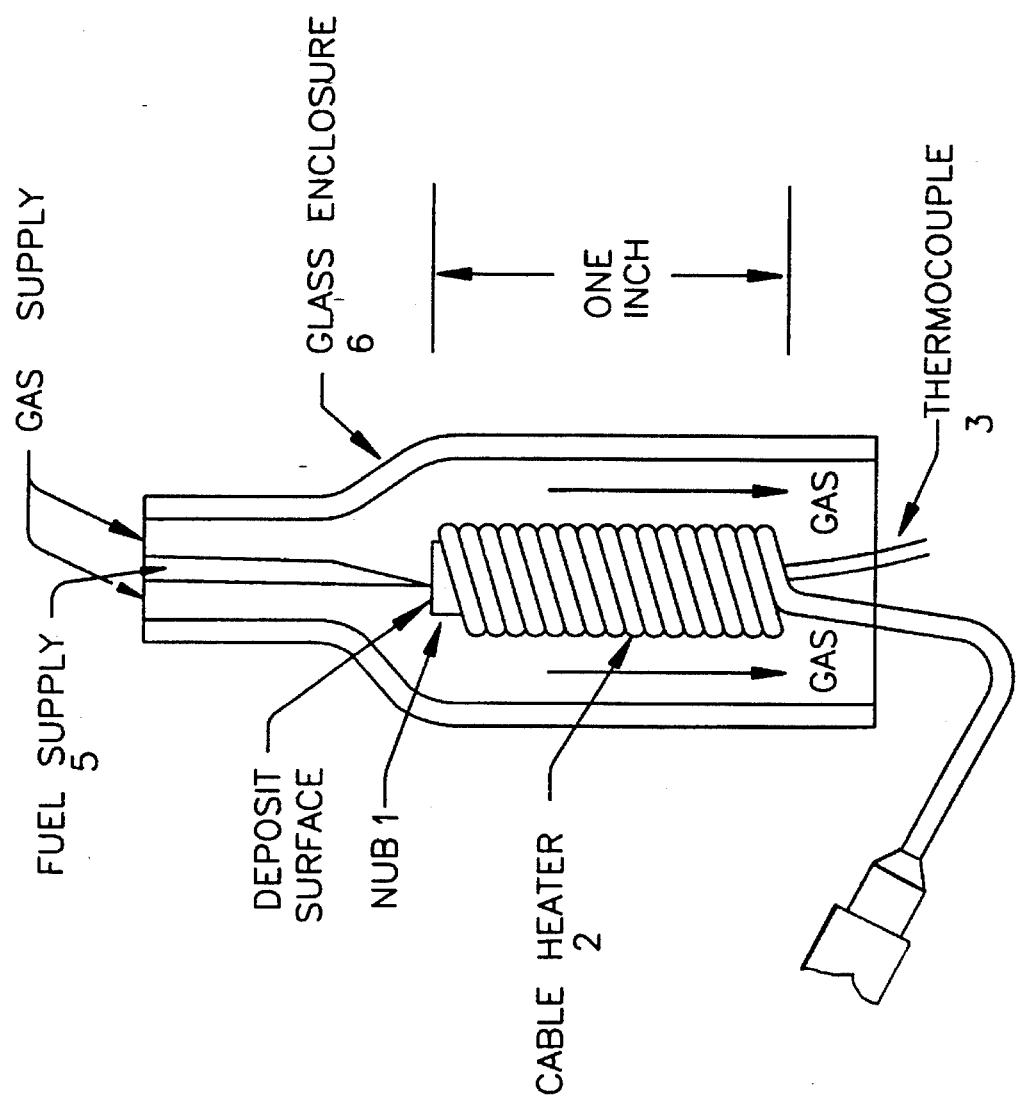

The system of the present invention is shown in FIGS. 1A and 1B. FIG. 1A shows a schematic view of the overall system. FIG. 1B shows an enlarged view of the nub [1] and thermocouple [3] arrangement. In the system, air [9] passes through a molecular sieve [10] which filters the air and removes contaminants. The air is dried by passing through silica gel [11]. The air is measured by the flow meter [12] and passes into the glass enclosure [6] where it combines with the fuel that is to be rated. Within the glass enclosure [6], the system includes a nub [1] inside the coils of a cable heater [2]. The "nub" is formed of a solid material. A convenient shape is a solid circular cylinder. However, the shape, surface topography, and material of the nub deposit surface can be varied to simulate various surfaces of a fuel system, including the intake system. Suitable materials include: steel, aluminum, and brass. A thermocouple is in close proximity with the nub depositing surface so as to control the nub surface temperature. A convenient way is to insert the thermocouple into a hole on the axis of the nub to a point under the deposit surface. The thermocouple [3] is used to control the deposit surface temperature. A novel feature of the present invention is that the deposit surface temperature is programmable [7]. With the aid of a transformer [13], the temperature can be steady or cycled through the range of temperatures encountered in engines during engine test cycles. The fuel is delivered by a syringe pump [4] to the deposit surface through a hypodermic needle [5]. Like deposit surface temperature, the fuel delivery rate can be programmed to emulate fuel delivery rates to surfaces in engine intake systems. A bell shaped glass enclosure [6] surrounds the nub and cable heater. It carries a blanketing flow of air [9], or any other desired gas, such as simulated exhaust gas to emulate exhaust gas recirculation in engines. The system may be operated without the gas bell in which case the deposits occur in air. The nub is weighed by the balance [8] before and after each run to determine the deposit mass accumulated onto the nub surface, which is typically 0.1 to 1.0 mg.

As shown in Examples below, the system can emulate intake system deposit formation. Other operating conditions can provide emulation of other deposit formation conditions. For example, the present invention can be used to study deposit formation from lubricants and to study deposit formation by ethanol fuel blends.

EXAMPLE 1

Figure 5:
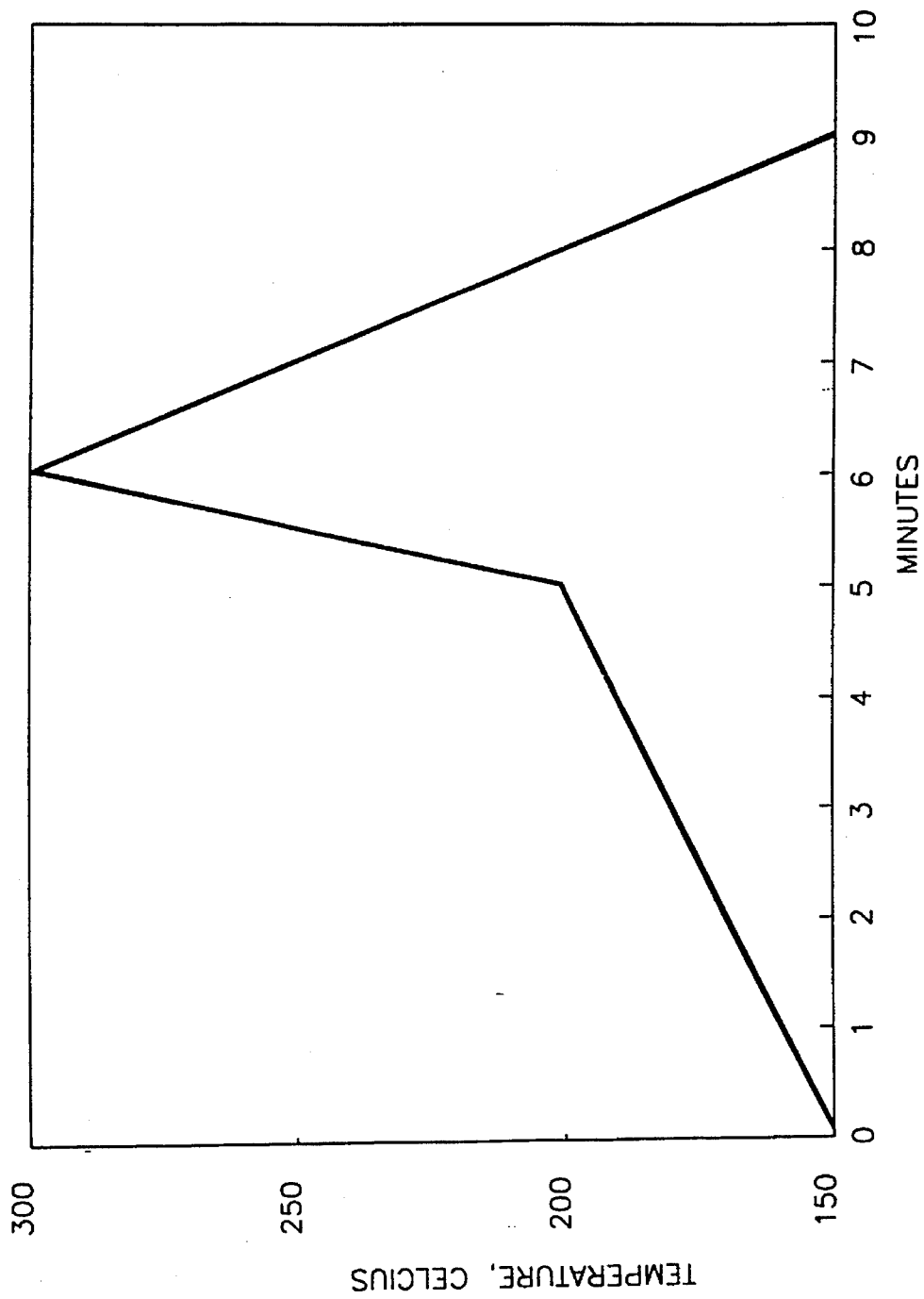
FIG. 5 shows a typical variation in temperature of the deposit surface in time for the present invention.

The Present Invention Emulates Effects of Fuel Composition on Engine Intake Valve Deposits The procedure for making the deposit is as follows. A syringe pump (FIG. 1a) delivered test gasoline at a steady flow of 10 mL/hr for a test duration of four hours. During the four hour test, the deposit surface temperature was programmed to vary as shown in FIG. 5. This temperature cycle was chosen to roughly emulate a gasoline engine. The nub was weighed before and after the test. The difference in the nub weight is the deposit, reported in units of milligrams per 100 mL of fuel used.

The same fuels were run through a conventional six cylinder gasoline engine for 100 hours. The deposits on the intake valves during this time were weighed in mg per valve.

Figure 2:
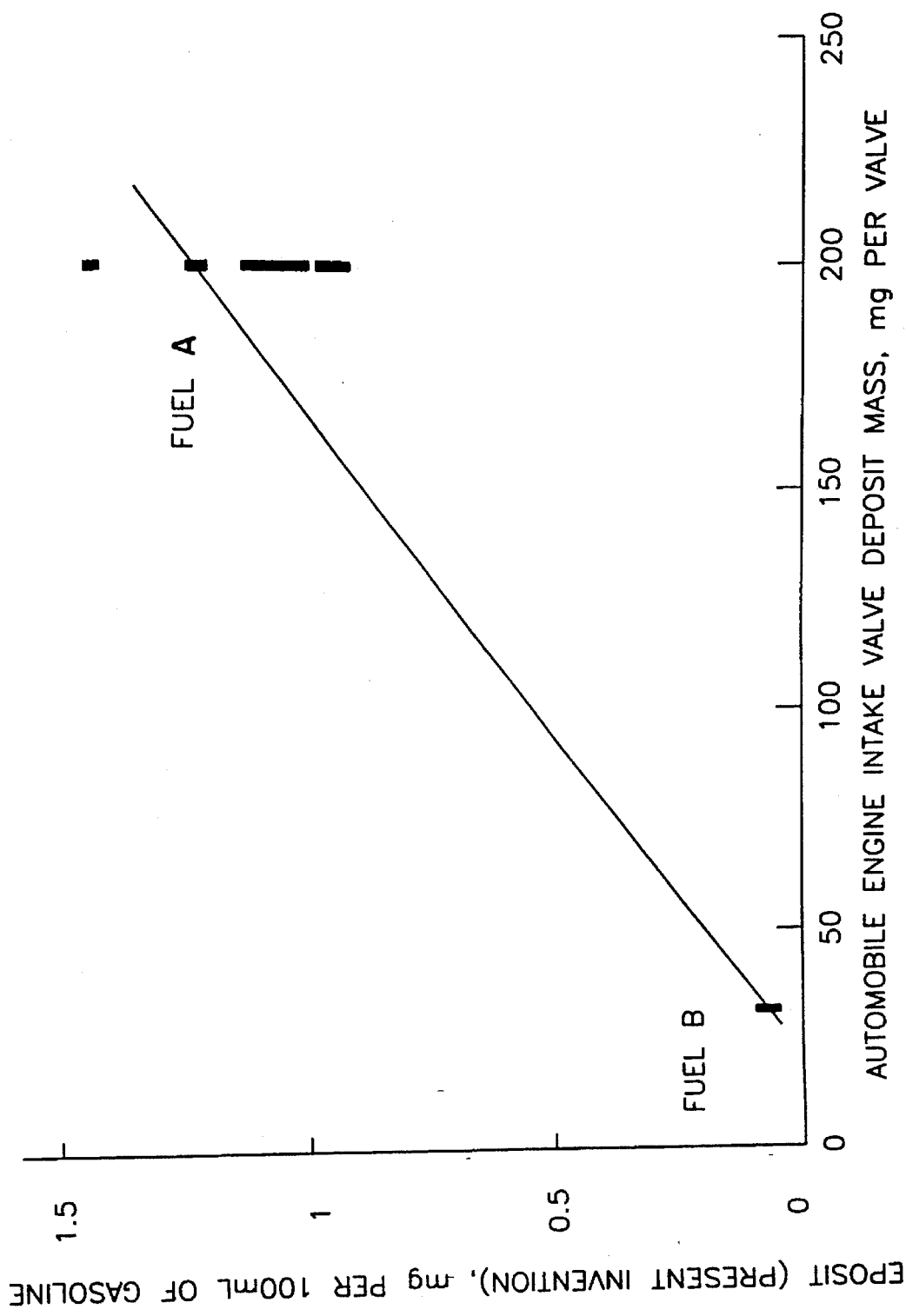
FIG. 2 shows a comparison of vehicle engine deposits with deposits using the present invention.

FIG. 2 shows that two fuels, A and B, were ranked by the present invention in the same order as the intake valve deposits in the gasoline engine. Fuel B was prepared by passing Fuel A through alumina, which removes molecules that are deposit precursors.

EXAMPLE 2

The Present Invention Emulates Effects of a Fuel Additive on Engine Intake Valve Deposits The experiment in Example 1 was repeated with fuel A and fuel A with a detergent fuel additive.

Figure 3:
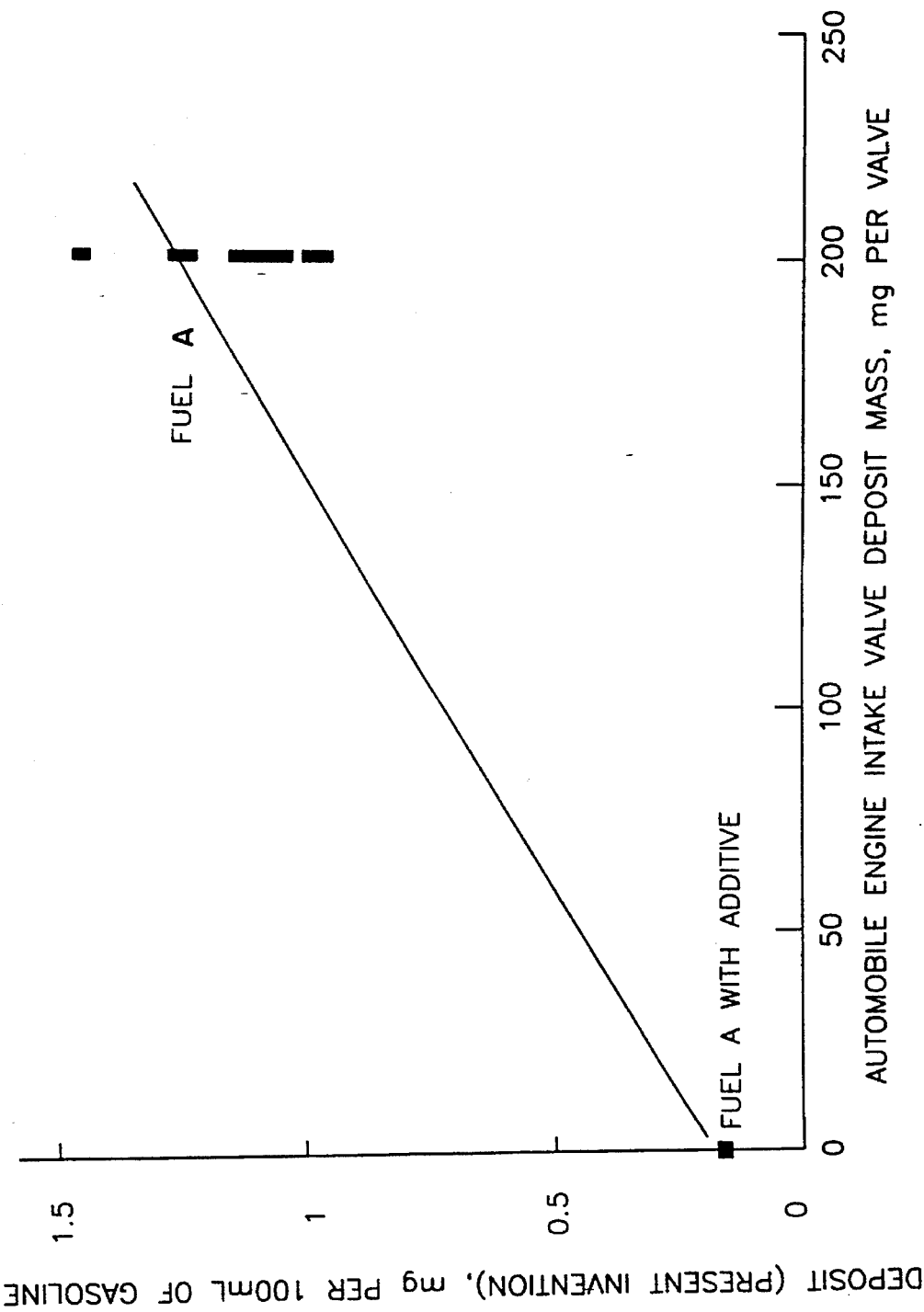
FIG. 3 shows a comparison of vehicle engine deposits with deposits from the present invention for a fuel with and without a deposit inhibiting additive.

FIG. 3 shows that a gasoline additive that reduces intake valve deposits in the gasoline engine also reduces deposits on the nub of the present invention.

EXAMPLE 3

Deposits Emulate the Chemical Composition of Engine Intake Valve Deposits

Another advantage of the present invention is that the nub and deposit are small enough that the deposit composition can be determined by advanced spectroscopic techniques without disturbing the deposit.

The chemical composition of the deposits was measured for fuel A in the nub deposit and the gasoline engine deposit.

Figure 4:
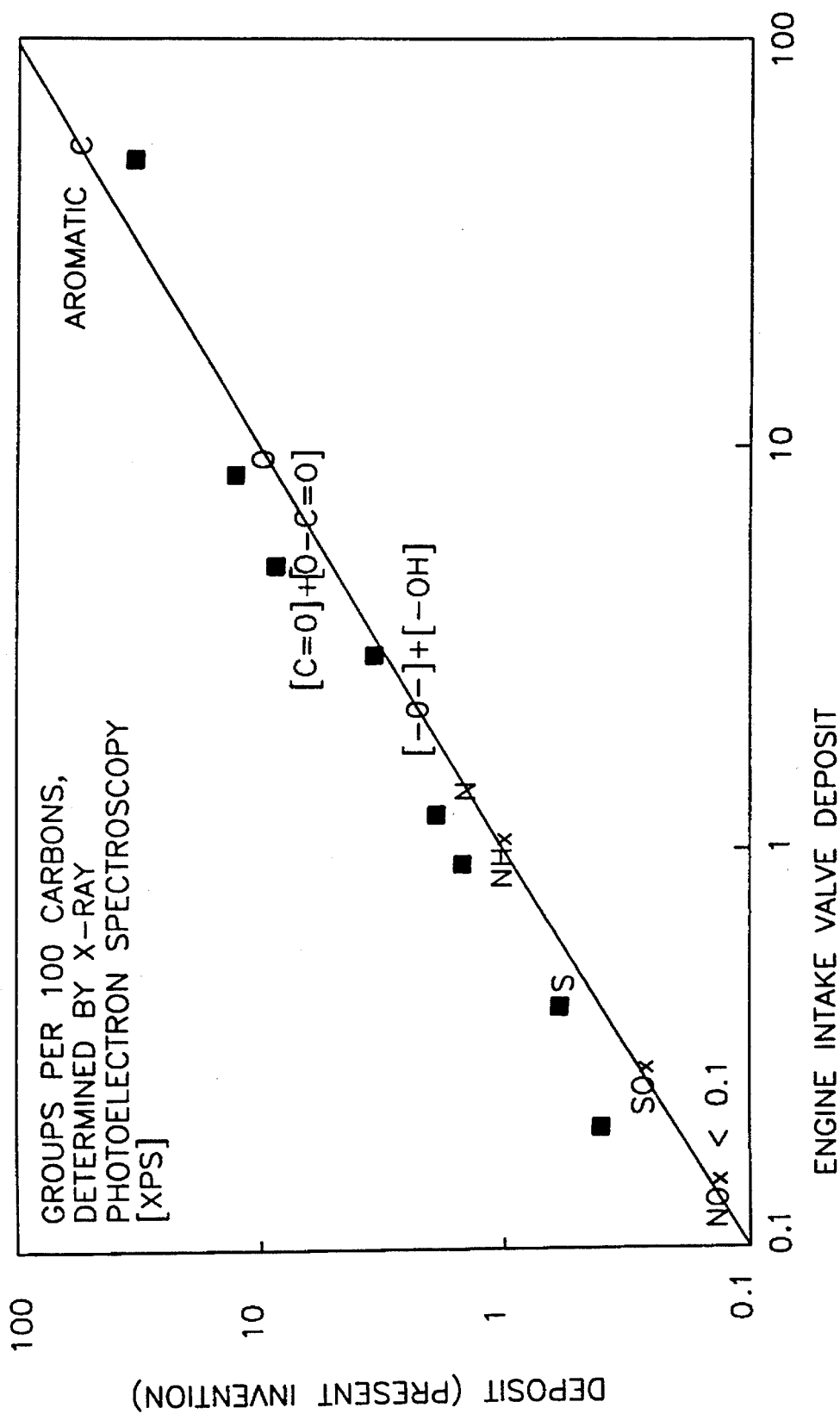
FIG. 4 shows a comparison of the amounts of several chemical groups in the deposits from a vehicle engine with the amounts in deposits from the present invention.

As shown in FIG. 4, the deposit on the nub in the system of the present invention has a chemical composition similar to engine intake valve deposit. The nub deposit has the same rank order of concentration of various molecular groups and elements as that of the intake valve deposit made with the same gasoline.

What is claimed is:

1. A system to rate fuels and fuel additives for the formation of deposits comprising:
   a) a solid nub having a deposit surface, having the contour of a surface used in an internal combustion engine
   b) means for introducing fuel and/or fuel additives onto said surface, so that fuel and/or fuel additives and resulting deposits do not move on said surface, and
   c) means for controlling the magnitude and duration of the temperature of said surface, such that the temperature of said surface emulates the temperature variation of a surface within an internal combustion engine, subjecting said stationary fuel and/or fuel additives and resulting deposits to said temperature variation.

2. The system of claim 1 further comprising a means for weighing said nub, before and after introduction of fuel and/or fuel additives to the deposit surface.

3. The system of claim 1 further comprising an enclosure and a means for introducing gas into said enclosure.

4. The system of claim 1 wherein said nub is steel, aluminum, brass or any solid material, or combination thereof.

5. The system of claim 1 wherein said depositing surface of said nub is shaped like surfaces of a fuel intake system of a vehicle engine and said nub is composed of materials used in fuel intake systems.

6. The system of claim 1 wherein said means to control temperature includes a heater, thermocouple and a temperature programmer.

7. The system of claim 1 wherein said means for introducing fuel and/or fuel additives including a syringe pump and a hypodermic needle.

8. The system of claim 3 wherein said enclosure is a glass bell shaped shield.

9. The system of claim 3 wherein said gas is air.

10. A method to rate fuels and fuel additives for the formation of deposits onto a solid having a surface of a given shape and material that conforms to any surface used in an internal combustion engine comprising:
    a) introducing fuel and/or fuel additives in controlled amounts onto said surface, so that fuel and/or fuel additives and resulting deposits do not move on said surface,
    b) controlling the magnitude and duration of the temperature of said surface, so that said temperature emulates the temperature variation of a surface within an internal combustion engine subjecting said fuel and/or fuel additives and resulting additives on said surfaces to said temperature variation, and
    c) weighing said solid before and after said introducing step to determine the amount of deposit onto said surface.

11. The method of claim 10 further comprising the step of enclosing said solid.

12. The method of claim 11 further comprising the step of injecting a gas into said enclosure.

* * * * *